United States Patent
Goto

(10) Patent No.: US 10,377,706 B2
(45) Date of Patent: Aug. 13, 2019

(54) METHOD FOR PRODUCING CARBOXYLIC ACID THIOESTER

(71) Applicant: Mitsubishi Chemical Corporation, Tokyo (JP)

(72) Inventor: Akihiro Goto, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 15/988,300

(22) Filed: May 24, 2018

(65) Prior Publication Data

US 2018/0265461 A1    Sep. 20, 2018

Related U.S. Application Data

(63) Continuation of application No. PCT/JP2016/084533, filed on Nov. 22, 2016.

(30) Foreign Application Priority Data

Nov. 26, 2015    (JP) .................. 2015-230365

(51) Int. Cl.
| | |
|---|---|
| C07C 327/06 | (2006.01) |
| C07C 327/22 | (2006.01) |
| C07C 327/24 | (2006.01) |
| C07C 327/26 | (2006.01) |
| C07C 327/32 | (2006.01) |
| C07D 213/70 | (2006.01) |
| C07C 327/08 | (2006.01) |
| C07D 277/74 | (2006.01) |
| C07B 61/00 | (2006.01) |

(52) U.S. Cl.
CPC .......... C07C 327/06 (2013.01); C07C 327/08 (2013.01); C07C 327/22 (2013.01); C07C 327/24 (2013.01); C07C 327/26 (2013.01); C07C 327/32 (2013.01); C07D 213/70 (2013.01); C07D 277/74 (2013.01); C07B 61/00 (2013.01); C07C 2601/14 (2017.05)

(58) Field of Classification Search
CPC .................................................. C07C 327/06
See application file for complete search history.

(56) References Cited

U.S. PATENT DOCUMENTS

| | | | | |
|---|---|---|---|---|
| 2013/0131370 A1* | 5/2013 | Hynes | ................... | C07C 253/30 558/256 |
| 2017/0088502 A1* | 3/2017 | Goto | ................... | C07C 51/56 |

FOREIGN PATENT DOCUMENTS

| | | | |
|---|---|---|---|
| JP | H05-286894 A | | 11/1993 |
| JP | H07-133252 A | | 5/1995 |
| JP | 2000-191590 A | | 7/2000 |
| JP | 2012-031090 A | | 2/2012 |
| JP | 2012031090 A | * | 2/2012 |
| JP | 2013-532641 A | | 8/2013 |
| WO | WO-2015186787 A1 | * | 12/2015 ............. C07C 51/56 |

OTHER PUBLICATIONS

Internet Archive WayBack Machine entry for https://www.sigmaaldrich.com/catalog/product/sigrna/m5671?lang=en&region=US dated Nov. 1, 2015, Sigma-Aldrich, Magnesium carbonate hydroxide pentahydrate (Year: 2015).*
Bartoli et al. Synthesis 2007, 22, 3489-3496 (Year: 2007).*
Sigma-Aldrich, Specification Sheet for magnesium chloride hexahydrate, Dec. 1995 (Year: 1995).*
International Search Report issued in related International Patent Application No. PCT/JP2016/084533 dated Jan. 24, 2017.
Du et al., "Crossed Intermolecular [2+2] Cycloadditions of Acyclic Enones via Visible Light Photocatalysis," Journal of the American Chemical Society, 131: 14604-14605 (2009).
Bartoli et al., "Reaction of Dicarbonates with Carboxylic Acids Catalyzed by Weak Lewis Acids: General Method for Synthesis of Anhydrides and Esters," Synthesis, 3489-3496 (2007).
Extended European Search Report issued in counterpart European Patent Application No. 16868528.7 dated Oct. 26, 2018.
Kim et al., "DI-2-Pyridyl Carbonate: A New Efficient Coupling Agent for the Direct Esterification of Carboxylic Acids," Tetrahedron Letters, 25: 4943-4946 (1984).

* cited by examiner

*Primary Examiner* — Matthew P Coughlin
(74) *Attorney, Agent, or Firm* — Morgan, Lewis & Bockius LLP

(57) ABSTRACT

According to the present invention, there is provided a method for producing carboxylic acid thioester, comprising reacting a compound represented by the following formula (I), carboxylic acid and thiol in the presence of a catalyst including at least one Group 2 metal compound. The production method is a production method which is simple in reaction operation, which places a small load on the environment and the human body and which enables carboxylic acid thioester to be catalytically obtained at a high yield even at a normal temperature and a normal pressure (25° C., 1 atm). In the formula (I), $R^1$ and $R^2$ each independently represent a hydrocarbon group having 1 to 20 carbon atoms.

(I)

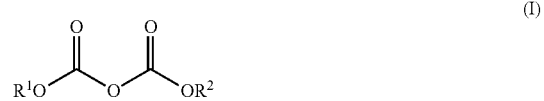

14 Claims, 2 Drawing Sheets

METHOD FOR PRODUCING CARBOXYLIC ACID THIOESTER

TECHNICAL FIELD

The present invention relates to a method for producing carboxylic acid thioester.

BACKGROUND ART

Carboxylic acid thioester is widely used as a synthetic raw material of a sulfur-containing compound in the fields of medicine, resin and the like. As a method for producing carboxylic acid thioester, there is known a method including reacting a highly reactive carboxylic acid derivative and thiol.

Patent Literature 1 describes a method for producing carboxylic acid thioester by reacting methacryloyl chloride and thiol in the presence of an aqueous sodium hydroxide solution and isopropyl acetate.

Non Patent Literature 1 describes a method for producing carboxylic acid thioester by reacting N,N'-dicyclohexylcarbodiimide, methacrylic acid and ethanethiol in the presence of 4-dimethylaminopyridine.

CITATION LIST

Patent Literature

Patent Literature 1: JP2012-31090A

Non Patent Literature

Non Patent Literature 1: J. Am. Chem. Soc., vol. 131, p. 14604 (2009)

SUMMARY OF INVENTION

Technical Problem

The method for producing carboxylic acid thioester described in Patent Literature 1, however, is economically handicapped and is inefficient because of using a large amount of a solvent. In addition, methacryloyl chloride is used as a substrate, and thus an equimolecular amount of hydrochloride or the like is produced as a by-product in a synthesis process. Furthermore, a washing step is incorporated in order to remove such a by-product. As a result, waste is produced as a by-product in a large amount, and thus such a method is economically handicapped and is also problematic in terms of environmental consequence. Additionally, thiol and methacryloyl chloride are each needed to be added into a reaction solution at 5° C. separately prepared, and therefore the operation is complicated and the method is also disadvantaged in terms of the reaction efficiency.

The method for producing carboxylic acid thioester described in Non Patent Literature 1 is economically handicapped and is inefficient because of using a large amount of a solvent. In addition, N,N'-dicyclohexylcarbodiimide is used as a substrate, and thus an equimolecular amount of 1,3-dicyclohexylurea or the like is produced as a by-product in a synthesis process. Furthermore, a washing step is incorporated in order to remove such a by-product. As a result, waste is produced as a by-product in a large amount, and thus such a method is economically handicapped and is also problematic in terms of environmental consequence.

Additionally, N,N'-dicyclohexylcarbodiimide causes allergic symptoms such as cough and rash, and therefore has the problem of placing a large load on the human body.

Accordingly, an object of the present invention is to provide a production method which is simple in reaction operation, which places a small load on the environment and the human body and which enables carboxylic acid thioester to be catalytically obtained at a high yield even at a normal temperature and a normal pressure (25° C., 1 atm).

Solution to Problem

The present inventors have made intensive studies in view of the problems of the related art, and as a result, have found that the above object can be achieved by performing a reaction in the presence of a specified catalyst, thereby leading to completion of the present invention. That is, the present invention provides the following [1] to [5].

[1] A method for producing carboxylic acid thioester, comprising reacting a compound represented by the following formula (I), carboxylic acid and thiol in the presence of a catalyst including at least one Group 2 metal compound. In the formula (I), $R^1$ and $R^2$ each independently represent a hydrocarbon group having 1 to 20 carbon atoms.

[Formula 1]

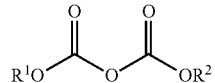

(I)

[2] The method for producing carboxylic acid thioester according to [1], wherein the catalyst further includes at least one Group 1 metal compound.

[3] The method for producing carboxylic acid thioester according to [1] or [2], wherein 0.1 to 10 mol of the compound represented by the formula (I) and 0.1 to 10 mol of the carboxylic acid per mol of the thiol are reacted.

[4] The method for producing carboxylic acid thioester according to any of [1] to [3], wherein the compound represented by the formula (I) is di-t-butyl dicarbonate.

[5] The method for producing carboxylic acid thioester according to any of [1] to [4], wherein the carboxylic acid is (meth)acrylic acid.

Advantageous Effects of Invention

The method for producing carboxylic acid thioester of the present invention can be performed even without use of a solvent. Thus, the method enables carboxylic acid thioester to be more efficiently and economically obtained than a conventional method. The method for producing carboxylic acid thioester of the present invention can produce carboxylic acid thioester by collectively placing raw materials. Thus, the method enables carboxylic acid thioester to be more efficiently and simply obtained than a conventional method. The method for producing carboxylic acid thioester of the present invention can produce carboxylic acid thioester by using raw materials low in risk and hazardousness. Thus, the method enables carboxylic acid thioester to be obtained with a smaller load on the human body than a conventional method. The method for producing carboxylic acid thioester of the present invention can catalytically provide carboxylic acid thioester at a high yield by use of a specified catalyst even at a normal temperature and a normal pressure (25° C., 1 atm). Thus, the method enables carboxylic acid thioester to be more efficiently and economically obtained with a smaller load on the environment than a conventional method.

DESCRIPTION OF EMBODIMENTS

Figure 1:
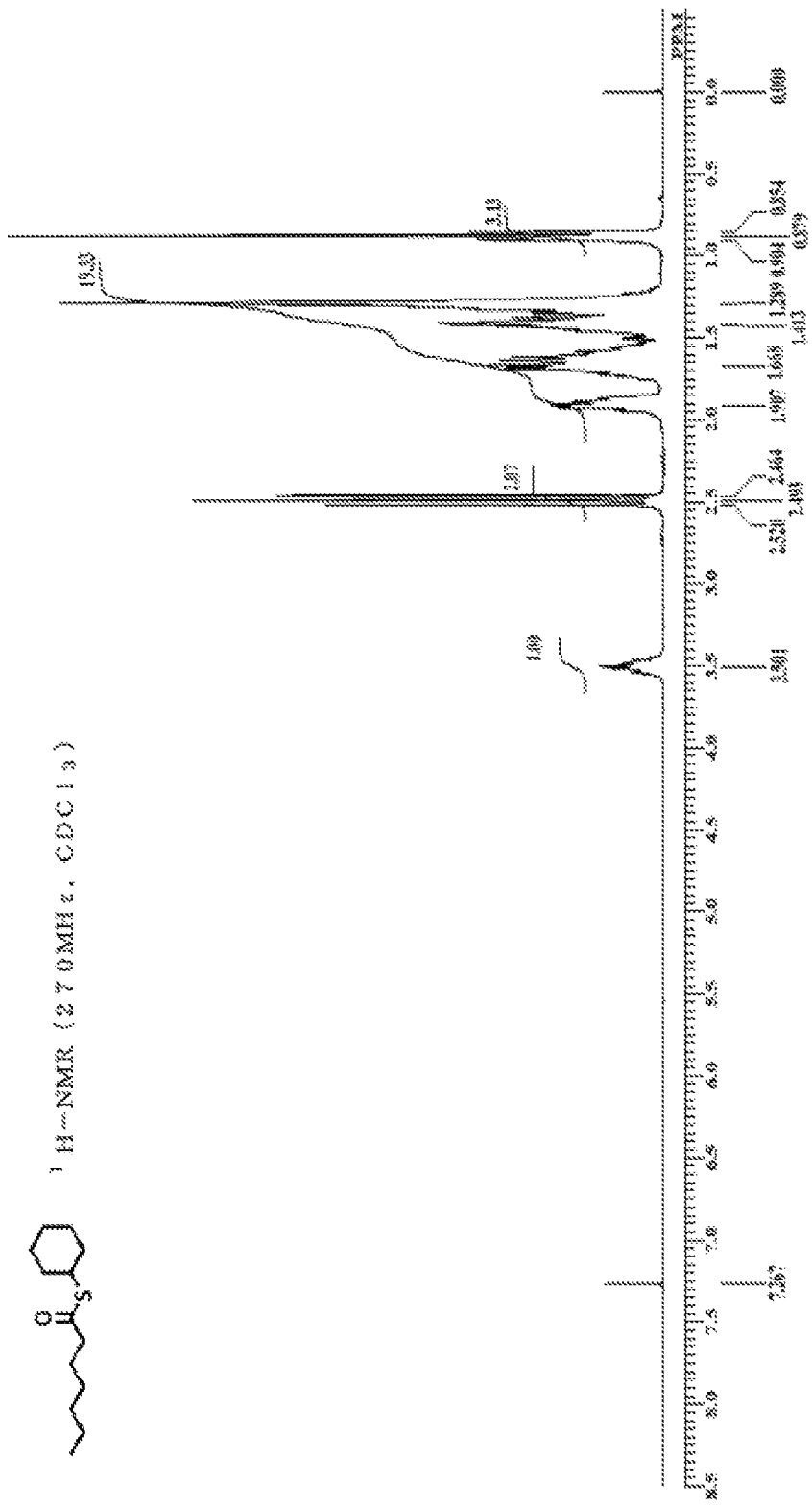
FIG. 1 illustrates a $^1$H-NMR spectrum of carboxylic acid thioester produced in each of Examples 53 and 54.

In the present description, acrylic acid and methacrylic acid are collectively designated as (meth)acrylic acid. In addition, acrylic acid thioester and methacrylic acid thioester are collectively designated as (meth)acrylic acid thioester.

[Compound Represented by Formula (I)]

In the method for producing carboxylic acid thioester of the present invention, a compound represented by the following formula (I) is used as a raw material. Herein, while the compound represented by the formula (I) produces an intermediate derived from the compound according to the reaction, carboxylic acid thioester finally obtained does not include any component derived from the compound.

[Formula 2]

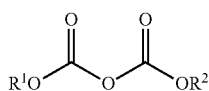

(I)

In the formula (I), $R^1$ and $R^2$ each independently represent a hydrocarbon group having 1 to 20 carbon atoms. Each of $R^1$ and $R^2$ is not limited in terms of the type and the structure thereof as long as it represents a hydrocarbon group. The hydrocarbon group may be linear or branched, or may have a ring structure. In addition, the hydrocarbon group may include an unsaturated bond or an ether bond. $R^1$ and $R^2$ may be bound to form a ring structure.

Examples of the hydrocarbon group represented by each of $R^1$ and $R^2$ include an alkyl group, an alkenyl group, an alkynyl group and an aryl group. The number of carbon atom(s) of each of such hydrocarbon groups is 1 to 20, preferably 2 to 10, more preferably 3 to 7 from the viewpoint of availability of the compound represented by the formula (I).

Examples of the hydrocarbon group represented by each of $R^1$ and $R^2$ can more specifically include an allyl group, a t-butyl group, a t-amyl group and a benzyl group. In addition, specific examples of the compound represented by the formula (I) include diallyl dicarbonate, di-t-butyl dicarbonate, di-t-amyl dicarbonate and dibenzyl dicarbonate. Among them, di-t-butyl dicarbonate where $R^1$ and $R^2$ each represent a t-butyl group is preferable because carboxylic acid thioester can be efficiently synthesized.

As the compound represented by the formula (I), a commercially available product can be used or one produced by a known method can be used. In addition, the compound represented by the formula (I) may be used singly or in combinations of two or more thereof.

The amount of the compound represented by the formula (I) to be used in the method for producing carboxylic acid thioester of the present invention is preferably 0.1 to 10 mol, more preferably 0.5 to 5 mol per mol of the thiol. The amount of the compound represented by the formula (I) to be used can be 0.1 mol or more per mol of the thiol, resulting in an increase in the yield of carboxylic acid thioester. In addition, the amount of the compound represented by the formula (I) to be used can be 10 mol or less per mol of the thiol, resulting in a decrease in the load on a post-treatment step after the reaction and an improvement in economic performance.

[Carboxylic Acid]

In the method for producing carboxylic acid thioester of the present invention, the type and the structure of the carboxylic acid as a raw material of carboxylic acid thioester are not limited. For example, the carboxylic acid can be represented by "$R^3$—COOH", and $R^3$ preferably represents a hydrocarbon group having 1 to 30 carbon atoms, optionally having a substituent. The hydrocarbon group may be linear or branched, or may have a ring structure. Furthermore, the hydrocarbon group may include an unsaturated bond or an ether bond. Herein, the phrase "optionally having a substituent" means that at least any one substituent is optionally included, and for example, means that at least one of the following bonds, groups and atoms is optionally included: an ester bond, an amide bond, an ether bond, a sulfide bond, a disulfide bond, a urethane bond, a nitro group, a cyano group, a ketone group, a formyl group, an acetal group, a thioacetal group, a sulfonyl group, a halogen atom, a silicon atom, a phosphorus atom and the like.

Examples of the hydrocarbon group represented by $R^3$ include an alkyl group, an alkenyl group, an alkynyl group and an aryl group. The number of carbon atom(s) of each of such hydrocarbon groups is preferably 1 to 30, more preferably 2 to 20 from the viewpoint of availability of the carboxylic acid.

Examples of the hydrocarbon group represented by $R^3$ can more specifically include a vinyl group, an isopropenyl group, a t-butyl group, a n-hexyl group, a cyclohexyl group, a phenyl group, a 2-chloroethyl group and a 4-(methoxycarbonyl)butyl group. Among them, $R^3$ preferably represents a vinyl group or an isopropenyl group. In addition, specific examples of the carboxylic acid include (meth)acrylic acid, pivalic acid, heptanoic acid, cyclohexanecarboxylic acid, benzoic acid, 3-chloropropionic acid and monomethyl adipate. Among them, the carboxylic acid is preferably (meth)acrylic acid.

As the carboxylic acid, a commercially available product can be used or one produced by a known method can be used. In addition, the carboxylic acid may be used singly or in combinations of two or more thereof. Furthermore, a polyvalent carboxylic acid such as adipic acid may be used as the carboxylic acid.

The amount of the carboxylic acid to be used in the method for producing carboxylic acid thioester of the present invention is preferably 0.1 to 10 mol, more preferably 0.5 to 5 mol per mol of the thiol. The amount of the carboxylic acid to be used can be 0.1 mol or more per mol of the thiol, resulting in an increase in the yield of carboxylic acid thioester. In addition, the amount of the carboxylic acid to be used can be 10 mol or less per mol of the thiol, resulting in a decrease in the load on a post-treatment step after the reaction and an improvement in economic performance.

[Thiol]

In the method for producing carboxylic acid thioester of the present invention, the type and the structure of the thiol as a raw material of carboxylic acid thioester are not limited.

For example, the thiol can be represented by "$R^4$—SH", and $R^4$ preferably represents a hydrocarbon group having 1 to 30 carbon atoms, optionally having a substituent. The hydrocarbon group may be linear or branched, or may have a ring structure. Furthermore, the hydrocarbon group may include an unsaturated bond. Herein, the phrase "optionally having a substituent" means that at least any one substituent is optionally included, and for example, means that at least one of the following bonds, groups and atoms is optionally included: an ester bond, an amide bond, an ether bond, a sulfide bond, a disulfide bond, a urethane bond, a nitro group, a cyano group, a ketone group, a formyl group, an acetal group, a thioacetal group, a sulfonyl group, a halogen atom, a silicon atom, a phosphorus atom and the like.

Examples of the hydrocarbon group represented by $R^4$ include an alkyl group, an alkenyl group, an alkynyl group and an aryl group. The number of carbon atom(s) of each of such hydrocarbon groups is preferably 1 to 30, more preferably 2 to 20 from the viewpoint of availability of the thiol.

Examples of the hydrocarbon group represented by $R^4$ can more specifically include a n-butyl group, a t-butyl group, a cyclohexyl group, a methoxycarbonylmethyl group, a phenyl group, a pyridyl group and a benzothiazolyl group. In addition, specific examples of the thiol include 1-butanethiol, t-butylmercaptan, cyclohexanethiol, methyl thioglycolate, benzenethiol, 2-mercaptopyridine and 2-mercaptobenzothiazole.

As the thiol, a commercially available product can be used or one produced by a known method can be used. In addition, the thiol may be used singly or in combinations of two or more thereof. Furthermore, a polyvalent thiol such as 1,4-butanedithiol may be used as the thiol.

[Catalyst]

The catalyst for use in the method for producing carboxylic acid thioester of the present invention includes at least one Group 2 metal compound from the viewpoint of being capable of efficiently synthesizing carboxylic acid thioester, and is preferably at least one Group 2 metal compound. Furthermore, at least one Group 2 metal compound and at least one Group 1 metal compound are more preferably used in combination in the catalyst. That is, the catalyst preferably includes at least one Group 2 metal compound and at least one Group 1 metal compound. The solubility of the catalyst varies depending on the ligand forming the catalyst, and therefore the catalyst can be used as a homogeneous catalyst or can be used as a heterogeneous catalyst.

In the method for producing carboxylic acid thioester of the present invention, the compound represented by the formula (I), the carboxylic acid and the thiol are reacted in the presence of the catalyst. Herein, the phrase "in the presence of the catalyst" means that the catalyst is present at at least one stage of the reaction process, and the catalyst is not necessarily always present at all the stages of the reaction process. Accordingly, the requirement "in the presence of the catalyst" is satisfied in the method for producing carboxylic acid thioester of the present invention as long as the catalyst is added to the reaction system. For example, even if the catalyst is somewhat changed during the reaction process after the catalyst is added to the reaction system, the requirement "in the presence of the catalyst" is satisfied.

(Group 2 Metal Compound)

The metal included in the Group 2 metal compound is not particularly limited, and magnesium, calcium, strontium and barium, among metals belonging to Group 2 of the periodic table, are preferable. Among them, magnesium and calcium are more preferable from the viewpoint of more enhancing the yield of carboxylic acid thioester.

Examples of the Group 2 metal compound include salts with inorganic acids, such as an oxide salt, a halide salt (chloride salt and the like), a hydroxide salt, a carbonate, a hydrogen carbonate, a silicate, a sulfate, an ammonium sulfate salt, a nitrate, a phosphate, a hydrogen phosphate, an ammonium phosphate salt, a borate, a halogenate, a perhalogenate, a halogenite and a hypohalite; salts with organic acids, such as a carboxylate (lactate, benzoate and the like), a percarboxylate and a sulfonate; and complex salts such as an acetylacetone salt, a hexafluoroacetylacetone salt, a porphyrin salt, a phthalocyanine salt and a cyclopentadiene salt. Such a salt may be any of a hydrate and an anhydrate, and is not particularly limited. Among them, an oxide salt, a chloride salt, a hydroxide salt, a nitrate, a phosphate, a carboxylate (lactate, benzoate and the like) and an acetylacetone salt are preferable, and an oxide salt, a chloride salt, a hydroxide salt, a carboxylate and an acetylacetone salt are more preferable, from the viewpoint of more enhancing the yield of carboxylic acid thioester.

As the Group 2 metal compound, a commercially available product can be used or one produced by a known method can be used. Such a compound may be used singly or in combinations of two or more thereof.

The amount of the Group 2 metal compound to be used is not particularly limited as long as carboxylic acid thioester can be produced. When only the Group 2 metal compound is used in the catalyst, the amount of the Group 2 metal compound to be used is preferably 0.01 to 1000 mol %, more preferably 0.05 to 500 mol %, relative to 1 mol of the thiol. When the Group 2 metal compound and a Group 1 metal compound described below are used in combination in the catalyst, the amount of the Group 2 metal compound to be used is preferably 0.001 to 1000 mol %, more preferably 0.005 to 500 mol %, relative to 1 mol of the thiol. The amount of the Group 2 metal compound to be used can be 0.001 mol % or more relative to 1 mol of the thiol, resulting in an increase in the yield of carboxylic acid thioester. The reason why the amount of the Group 2 metal compound to be used is 1000 mol % or less relative to 1 mol of the thiol is because a significant enhancement of the effect is hardly expected even if the amount is more than 1000 mol %. Herein, when two or more Group 2 metal compounds are used, the total amount thereof to be used may be within the above range.

(Group 1 Metal Compound)

The metal included in the Group 1 metal compound is not particularly limited, and lithium, sodium, potassium, rubidium and cesium, among metals belonging to Group 1 of the periodic table, are preferable.

Examples of the Group 1 metal compound include salts with inorganic acids, such as a hydride salt, an oxide salt, a halide salt (chloride salt and the like), a hydroxide salt, a carbonate, a hydrogen carbonate, a sulfate, a nitrate, a phosphate, a borate, a halogenate, a perhalogenate, a halogenite, a hypohalite and a thiocyanate; salts with organic acids, such as an alkoxide salt, a carboxylate (acetate and the like) and a sulfonate (trifluoromethanesulfonate and the like); salts with organic bases, such as an amide salt, a sulfoneamide salt and a sulfoneimide salt (bis(trifluoromethanesulfonyl)imide salt and the like); and complex salts such as an acetylacetone salt, a hexafluoroacetylacetone salt, a porphyrin salt, a phthalocyanine salt and a cyclopentadiene salt. Such a salt may be any of a hydrate and an anhydrate, and is not particularly limited.

As the Group 1 metal compound, a commercially available product can be used or one produced by a known method can be used. Such a compound may be used singly or in combinations of two or more thereof.

The amount of the Group 1 metal compound to be used is not particularly limited as long as carboxylic acid thioester can be produced. The amount of the Group 1 metal compound to be used is preferably 0.001 to 1000 mol %, more preferably 0.005 to 500 mol %, relative to 1 mol of the thiol. The amount of the Group 1 metal compound to be used can be 0.001 mol % or more relative to 1 mol of the thiol, resulting in an increase in the yield of carboxylic acid thioester. The reason why the amount of the Group 1 metal compound to be used is 1000 mol % or less per mol of the thiol is because a significant enhancement of the effect is hardly expected even if the amount is more than 1000 mol %. Furthermore, when the Group 2 metal compound and the Group 1 metal compound are used in combination, the amount of the Group 1 metal compound to be used is preferably 0.01 to 50 mol, more preferably 0.05 to 10 mol, further preferably 0.05 to 7 mol relative to 1 mol of the Group 2 metal compound. The amount of the Group 1 metal compound to be used can be 0.01 mol or more relative to 1 mol of the Group 2 metal compound, resulting in an increase in the yield of carboxylic acid thioester. The reason why the amount of the Group 1 metal compound to be used is 50 mol or less per mol of the Group 2 metal compound is because a significant enhancement of the effect is hardly expected even if the amount is more than 50 mol. Herein, when two or more Group 1 metal compounds are used, the total amount thereof to be used may be within the above range.

[Reaction Conditions]

The reaction conditions in the method for producing carboxylic acid thioester of the present invention are not particularly limited, and the reaction conditions can also be appropriately modified in the reaction process. The form of a reaction container for use in the reaction is not particularly limited.

The reaction temperature is not particularly limited, can be, for example, −20 to 180° C., and is preferably 0 to 100° C. The reaction temperature can be −20° C. or more, thereby allowing the reaction to efficiently progress. In addition, the reaction temperature can be 180° C. or less, thereby decreasing the amount of a by-product and suppressing coloration of the reaction liquid.

The reaction time is not particularly limited, can be, for example, 0.5 to 72 hours, and is preferably 2 to 48 hours. The reaction time can be 0.5 hours or more, thereby allowing the reaction to sufficiently progress. In addition, the reason why the reaction time is 72 hours or less is because a significant enhancement of the effect is hardly expected even if the reaction time is more than 72 hours.

The reaction atmosphere and the reaction pressure are also not particularly limited.

The production of carboxylic acid thioester of the present invention can be conducted in the absence of a solvent (without use of a solvent). When the viscosity of the reaction liquid is high, a solvent can be, if necessary, used. The type of the solvent is not particularly limited, and, for example, an organic compound having 1 to 25 carbon atoms can be used and can be appropriately selected depending on the reaction conditions. Examples of the organic compound having 1 to 25 carbon atoms include ethers such as 1,4-dioxane, hydrocarbons such as toluene, and halogenated hydrocarbons such as dichloromethane. Such a solvent may be used singly or as a mixture of two or more of such solvents. The amount of the solvent to be used is also not particularly limited, and can be appropriately selected.

The method of introducing raw materials (the compound represented by the formula (I), the carboxylic acid and the thiol) for use in the reaction, as well as the catalyst, the solvent and the like into the reaction container is not particularly limited, and all the raw materials and the like may be collectively introduced, the raw materials and the like may be partially or fully introduced in a stepwise manner, or the raw materials and the like may be partially or fully introduced in a continuous manner. In addition, an introduction method where such manners are combined may also be adopted.

[Carboxylic Acid Thioester]

The product obtained in the method for producing carboxylic acid thioester of the present invention can be represented by "$R^3COSR^4$". Herein, $R^3$ and $R^4$ are as described in the description section of the carboxylic acid and the description section of the thiol, respectively.

When the carboxylic acid for use in the method for producing carboxylic acid thioester of the present invention is (meth)acrylic acid, (meth)acrylic acid thioester is produced. (Meth)acrylic acid and (meth)acrylic acid thioester are compounds to be easily polymerized, and therefore a polymerization inhibitor may be added in advance in order to prevent polymerization. The timing where the polymerization inhibitor is added is not particularly limited, and the polymerization inhibitor is preferably added at the start of the reaction from the viewpoint of ease of operation.

The type of the polymerization inhibitor to be used is not particularly limited, and a known polymerization inhibitor such as a 2,2,6,6-tetramethyl piperidine 1-oxyl free radical can be used. Such a polymerization inhibitor may be used singly or in combinations of two or more thereof. When the polymerization inhibitor is added, the amount of the polymerization inhibitor to be used is preferably 0.001 to 0.5 parts by mass, more preferably 0.01 to 0.1 parts by mass relative to 100 parts by mass of (meth)acrylic acid or (meth)acrylic acid thioester. In addition, an oxygen-containing gas such as air may be blown. The amount of the gas to be blown can be appropriately selected depending on the reaction conditions.

In the method for producing carboxylic acid thioester of the present invention, the resulting carboxylic acid thioester may be used in the next reaction as it is or may be, if necessary, purified. The purification conditions are not particularly limited, and the purification conditions can be appropriately modified during the reaction process and at the end of the reaction. For example, after completion of the reaction, the carboxylic acid thioester can be purified from the resulting reaction mixture liquid by a method such as filtration, distillation under reduced pressure, chromatography and recrystallization. Such a purification method can be used singly or in combinations thereof.

In the method for producing carboxylic acid thioester of the present invention, the preservation container of the resulting carboxylic acid thioester is not particularly limited, and, for example, a glass container, a resin container, a metallic storage tank, a drum can, a tanker or the like can be used.

EXAMPLES

Hereinafter, the present invention is specifically described with reference to Examples, but the present invention is not intended to be limited to only these Examples and can be arbitrarily modified and carried out without departing from the gist of the present invention.

The di-t-butyl dicarbonate used in the following Examples and Comparative Examples is a compound having a purity of 98% by mass, produced by Tokyo Chemical Industry Co., Ltd., in which $R^1$ and $R^2$ in the formula (I) each represent a t-butyl group. In addition, the method of measuring the yield of a product is as follows.

After completion of the reaction, a standard substance (anisole or 1,1,2,2-tetrachloroethane) was added to the resulting reaction mixture liquid, and these were dissolved in deuterochloroform ($CDCl_3$) and subjected to $^1$H-NMR (270 MHz) measurement. The amount of substance (mol) of carboxylic acid thioester produced was determined by conversion of the integrated value of the resulting spectrum. Next, the yield of the carboxylic acid thioester was calculated from the following expression (1) (when the yield calculated was less than 1%, however, the yield was expressed as 0).

Yield of carboxylic acid thioester (%)=$(P_1/S_1)\times 100$     (1)

$P_1$: amount of substance (mol) of carboxylic acid thioester produced $S_1$: amount of substance (mol) of thiol used In addition, the amount (mol %) of each of the Group 2 metal compound and the Group 1 metal compound as the catalyst was calculated according to the following expression (2).

Amount of catalyst added (mol %)=$(C_1$ or $C_2/S_1)\times 100$     (2)

$C_1$: amount of substance (mol) of Group 2 metal compound used $C_2$: amount of substance (mol) of Group 1 metal compound used $S_1$: amount of substance (mol) of thiol used In addition, the molar equivalent of each of the compound represented by the formula (I) and the carboxylic acid as raw materials was calculated according to the following expression (3).

Molar equivalent of raw materials=$(S_3$ or $S_2/S_1)$     (3)

$S_3$: amount of substance (mol) of compound represented by formula (I)

$S_2$: amount of substance (mol) of carboxylic acid used $S_1$: amount of substance (mol) of thiol used Example 1

Into an eggplant flask having a volume of 200 mL were sequentially added 12.430 g (95.48 mmol) of heptanoic acid, 21.263 g (95.48 mmol) of di-t-butyl dicarbonate, 8.200 g (90.93 mmol) of 1-butanethiol and 0.027 g (0.45 mmol, 0.5 mol % relative to 1 mol of 1-butanethiol) of magnesium hydroxide, and the reaction was carried out at 25° C. with stirring to produce S-butyl thioheptanoate. The reaction results after 24 hours from the start of the reaction are shown in Table 1.

Examples 2 to 67 and Comparative Examples 1 to 6

Each carboxylic acid thioester was produced in the same manner as in Example 1 except that raw materials, a metal compound and a solvent described in Tables 1 to 7 were used, and the amounts used and the conditions were changed as described in the Tables. The reaction results after 3 to 48 hours from the start of the reaction are each shown in Tables 1 to 7.

Figure 2:
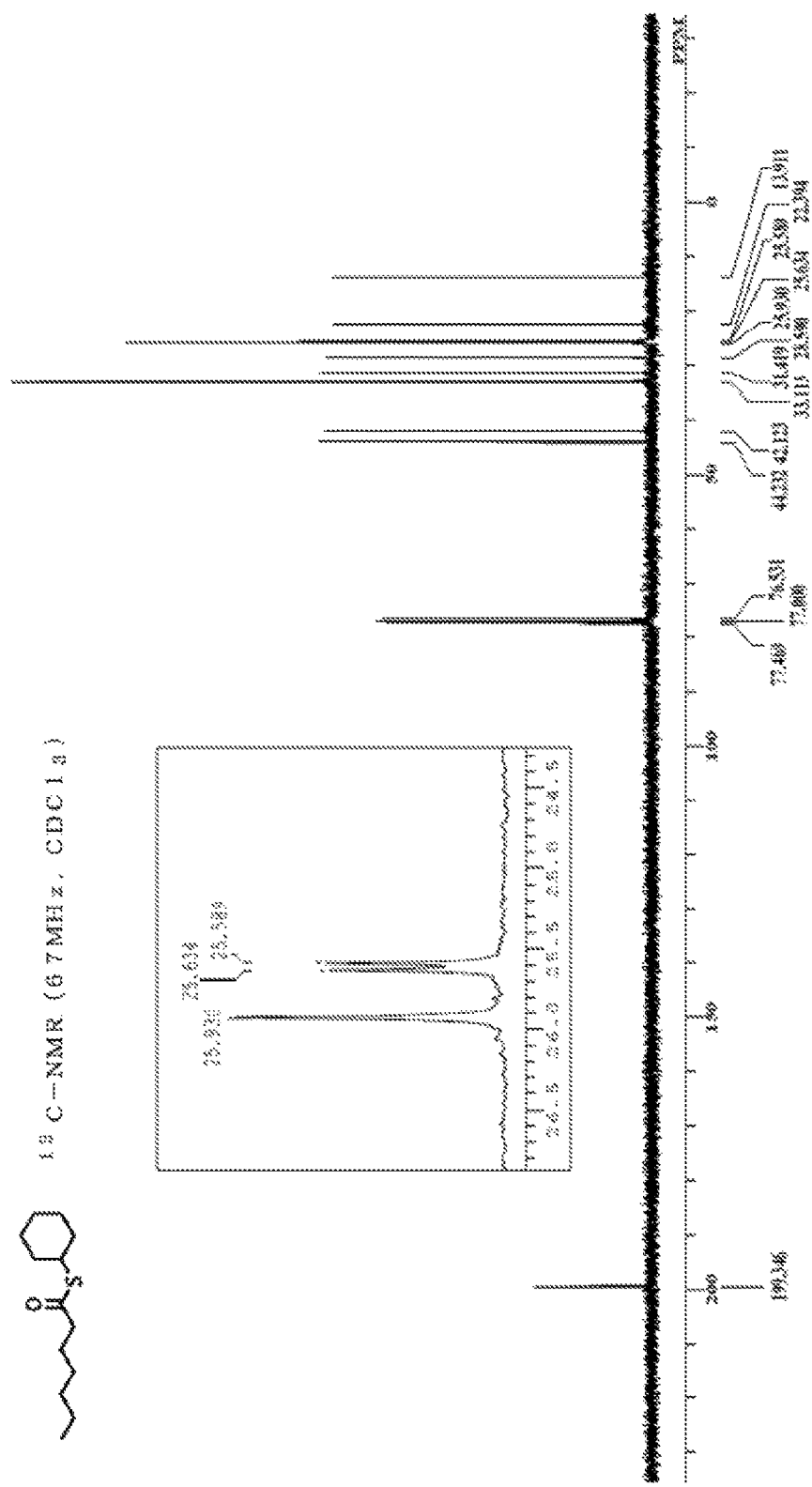
FIG. 2 illustrates a $^{13}$C-NMR spectrum of carboxylic acid thioester produced in each of Examples 53 and 54.

A $^1$H-NMR spectrum and a $^{13}$C-NMR spectrum of the carboxylic acid thioester produced in each of Examples 53 and 54 are illustrated in FIG. 1 and FIG. 2, respectively.

The carboxylic acid thioester produced in Example 64 is represented by the following formula (II) and the following formula (III).

[Formula 3]

(II)

[Formula 3]

(III)

The yield of each of carboxylic acid thioesters (II) and (III) was calculated according to the following expression (4).

Yield of carboxylic acid thioester (%)=$(P_1/S_2)\times 100$     (4)

$P_1$: amount of substance (mol) of carboxylic acid thioester (II) or (III) produced $S_2$: amount of substance (mol) of adipic acid used

TABLE 1

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 1 | Di-t-butyl dicarbonate (1.05) | Heptanoic acid (1.05) | 1-Butanethiol (0.091) | Magnesium hydroxide | 0.5 | — | — | — | 25 | 24 | 8 |
| Example 2 | Di-t-butyl dicarbonate (1.05) | Heptanoic acid (1.05) | 1-Butanethiol (0.091) | Magnesium hydroxide | 3.0 | — | — | — | 25 | 24 | 62 |
| Example 3 | Di-t-butyl dicarbonate (1.05) | Heptanoic acid (1.05) | 1-Butanethiol (0.055) | Magnesium oxide | 3.0 | — | — | — | 25 | 24 | 81 |
| Example 4 | Di-t-butyl dicarbonate (1.05) | Heptanoic acid (1.05) | 1-Butanethiol (0.055) | Magnesium nitrate hexahydrate | 3.0 | — | — | — | 25 | 24 48 | 0 1 |

TABLE 1-continued

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 5 | Di-t-butyl dicarbonate (1.05) | Heptanoic acid (1.05) | 1-Butanethiol (0.055) | Magnesium phosphate octahydrate | 3.0 | — | — | — | 25 | 24<br>48 | 6<br>13 |
| Example 6 | Di-t-butyl dicarbonate (1.05) | Heptanoic acid (1.05) | 1-Butanethiol (0.055) | Magnesium chloride | 3.0 | — | — | — | 25 | 24 | 60 |
| Example 7 | Di-t-butyl dicarbonate (1.05) | Heptanoic acid (1.05) | 1-Butanethiol (0.055) | Magnesium benzoate trihydrate | 3.0 | — | — | — | 25 | 24 | 71 |
| Example 8 | Di-t-butyl dicarbonate (1.05) | Heptanoic acid (1.05) | 1-Butanethiol (0.055) | Magnesium lactate trihydrate | 3.0 | — | — | — | 25 | 24 | 34 |
| Example 9 | Di-t-butyl dicarbonate (1.05) | Heptanoic acid (1.05) | 1-Butanethiol (0.055) | Acetylacetone magnesium | 3.0 | — | — | — | 25 | 24<br>48 | 4<br>9 |
| Example 10 | Di-t-butyl dicarbonate (1.05) | Heptanoic acid (1.05) | 1-Butanethiol (0.055) | Calcium hydroxide | 3.0 | — | — | — | 25 | 24<br>48 | 10<br>18 |
| Example 11 | Di-t-butyl dicarbonate (1.05) | Heptanoic acid (1.05) | 1-Butanethiol (0.055) | Calcium oxide | 3.0 | — | — | — | 25 | 24<br>48 | 8<br>25 |
| Example 12 | Di-t-butyl dicarbonate (1.05) | Heptanoic acid (1.05) | 1-Butanethiol (0.055) | Strontium oxide | 3.0 | — | — | — | 25 | 24<br>48 | 1<br>5 |
| Example 13 | Di-t-butyl dicarbonate (1.05) | Heptanoic acid (1.05) | 1-Butanethiol (0.055) | Barium oxide | 3.0 | — | — | — | 25 | 24<br>48 | 0<br>1 |

TABLE 2

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 14 | Di-t-butyl dicarbonate (1.05) | Heptanoic acid (1.05) | 1-Butanethiol (0.182) | Magnesium hydroxide | 0.5 | Lithium hydroxide monohydrate | 0.125 | — | 25 | 3<br>5<br>7<br>24 | 10<br>29<br>54<br>83 |
| Example 15 | Di-t-butyl dicarbonate (1.05) | Heptanoic acid (1.05) | 1-Butanethiol (0.091) | Magnesium hydroxide | 0.5 | Lithium hydroxide monohydrate | 0.25 | — | 25 | 3<br>5<br>7<br>24 | 37<br>56<br>75<br>>99 |
| Example 16 | Di-t-butyl dicarbonate (1.05) | Heptanoic acid (1.05) | 1-Butanethiol (0.091) | Magnesium hydroxide | 0.5 | Lithium hydroxide monohydrate | 0.5 | — | 25 | 3<br>5<br>7<br>24 | 28<br>53<br>67<br>99 |
| Example 17 | Di-t-butyl dicarbonate (1.05) | Heptanoic acid (1.05) | 1-Butanethiol (0.091) | Magnesium hydroxide | 0.5 | Lithium hydroxide monohydrate | 1.0 | — | 25 | 3<br>5<br>7<br>24 | 11<br>34<br>52<br>92 |
| Example 18 | Di-t-butyl dicarbonate (1.05) | Heptanoic acid (1.05) | 1-Butanethiol (0.091) | Magnesium hydroxide | 0.5 | Lithium hydroxide monohydrate | 2.0 | — | 25 | 3<br>5<br>7<br>24 | 1<br>3<br>5<br>18 |
| Example 19 | Di-t-butyl dicarbonate (1.05) | Heptanoic acid (1.05) | 1-Butanethiol (0.091) | Magnesium hydroxide | 0.5 | Lithium hydroxide monohydrate | 4.0 | — | 25 | 3<br>5<br>7<br>24 | 0<br>1<br>1<br>6 |

TABLE 3

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 20 | Di-t-butyl dicarbonate (1.05) | Heptanoic acid (1.05) | 1-Butane-thiol (0.055) | Magnesium hydroxide | 0.5 | Sodium hydroxide | 0.5 | — | 25 | 24 | >99 |
| Example 21 | Di-t-butyl dicarbonate (1.05) | Heptanoic acid (1.05) | 1-Butane-thiol (0.055) | Magnesium hydroxide | 0.5 | Cesium hydroxide monohydrate | 0.5 | — | 25 | 24 | 43 |
| Example 22 | Di-t-butyl dicarbonate (1.05) | Heptanoic acid (1.05) | 1-Butane-thiol (0.055) | Magnesium hydroxide | 0.5 | Lithium oxide | 0.5 | — | 25 | 24 | 88 |
| Example 23 | Di-t-butyl dicarbonate (1.05) | Heptanoic acid (1.05) | 1-Butane-thiol (0.055) | Magnesium hydroxide | 0.5 | Lithium carbonate | 0.5 | — | 25 | 24 | 70 |
| Example 24 | Di-t-butyl dicarbonate (1.05) | Heptanoic acid (1.05) | 1-Butane-thiol (0.055) | Magnesium hydroxide | 0.5 | Sodium carbonate | 0.5 | — | 25 | 24 | >99 |
| Example 25 | Di-t-butyl dicarbonate (1.05) | Heptanoic acid (1.05) | 1-Butane-thiol (0.055) | Magnesium hydroxide | 0.5 | Potassium carbonate | 0.5 | — | 25 | 24 | 60 |
| Example 26 | Di-t-butyl dicarbonate (1.05) | Heptanoic acid (1.05) | 1-Butane-thiol (0.055) | Magnesium hydroxide | 0.5 | Rubidium carbonate | 0.5 | — | 25 | 24 | 42 |
| Example 27 | Di-t-butyl dicarbonate (1.05) | Heptanoic acid (1.05) | 1-Butane-thiol (0.055) | Magnesium hydroxide | 0.5 | Cesium carbonate | 0.5 | — | 25 | 24 | 25 |
| Example 28 | Di-t-butyl dicarbonate (1.05) | Heptanoic acid (1.05) | 1-Butane-thiol (0.055) | Magnesium hydroxide | 0.5 | Sodium hydrogen carbonate | 0.5 | — | 25 | 24 | 85 |
| Example 29 | Di-t-butyl dicarbonate (1.05) | Heptanoic acid (1.05) | 1-Butane thiol (0.055) | Magnesium hydroxide | 0.5 | Sodium sulfate | 0.5 | — | 25 | 24 | 41 |
| Example 30 | Di-t-butyl dicarbonate (1.05) | Heptanoic acid (1.05) | 1-Butane-thiol (0.055) | Magnesium hydroxide | 0.5 | Lithium chloride | 0.5 | — | 25 | 24 | 95 |

TABLE 4

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 31 | Di-t-butyl dicarbonate (1.05) | Heptanoic acid (1.05) | 1-Butane-thiol (0.055) | Magnesium hydroxide | 0.5 | Sodium chloride | 0.5 | — | 25 | 24 | 17 |
| Example 32 | Di-t-butyl dicarbonate (1.05) | Heptanoic acid (1.05) | 1-Butane-thiol (0.055) | Magnesium hydroxide | 0.5 | Potassium chloride | 0.5 | — | 25 | 24 | 25 |
| Example 33 | Di-t-butyl dicarbonate (1.05) | Heptanoic acid (1.05) | 1-Butane-thiol (0.055) | Magnesium hydroxide | 0.5 | Rubidium chloride | 0.5 | — | 25 | 24 | 44 |
| Example 34 | Di-t-butyl dicarbonate (1.05) | Heptanoic acid (1.05) | 1-Butane-thiol (0.055) | Magnesium hydroxide | 0.5 | Cesium chloride | 0.5 | — | 25 | 24 | 33 |
| Example 35 | Di-t-butyl dicarbonate (1.05) | Heptanoic acid (1.05) | 1-Butane-thiol (0.055) | Magnesium hydroxide | 0.5 | Lithium acetate | 0.5 | — | 25 | 24 | 96 |
| Example 36 | Di-t-butyl dicarbonate (1.05) | Heptanoic acid (1.05) | 1-Butane-thiol (0.055) | Magnesium hydroxide | 0.5 | Lithium trifluoro-methane-sulfonate | 0.5 | — | 25 | 24 | 82 |
| Example 37 | Di-t-butyl dicarbonate (1.05) | Heptanoic acid (1.05) | 1-Butane thiol (0.055) | Magnesium hydroxide | 0.5 | Lithium amide | 0.5 | — | 25 | 24 | 97 |
| Example 38 | Di-t-butyl dicarbonate (1.05) | Heptanoic acid (1.05) | 1-Butane-thiol (0.055) | Magnesium hydroxide | 0.5 | Lithium bis(tri-fluoro-methane-sulfon-yl)imide | 0.5 | — | 25 | 24 | 71 |

TABLE 4-continued

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 39 | Di-t-butyl dicarbonate (1.05) | Heptanoic acid (1.05) | 1-Butanethiol (0.055) | Magnesium hydroxide | 0.5 | Acetylacetone lithium | 0.5 | — | 25 | 24 | 94 |
| Example 40 | Di-t-butyl dicarbonate (1.05) | Heptanoic acid (1.05) | 1-Butanethiol (0.055) | Magnesium hydroxide | 0.5 | Lithium bis(oxalate)borate | 0.5 | — | 25 | 24 | 68 |
| Example 41 | Di-t-butyl dicarbonate (1.05) | Heptanoic acid (1.05) | 1-Butanethiol (0.055) | Magnesium hydroxide | 0.5 | Sodium phosphate | 0.5 | — | 25 | 24 | >99 |

TABLE 5

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 42 | Di-t-butyl dicarbonate (1.05) | Heptanoic acid (1.05) | 1-Butanethiol (0.055) | Magnesium oxide | 3.0 | Lithium hydroxide monohydrate | 3.0 | — | 25 | 24 | 93 |
| Example 43 | Di-t-butyl dicarbonate (1.05) | Heptanoic acid (1.05) | 1-Butanethiol (0.055) | Magnesium nitrate hexahydrate | 3.0 | Lithium hydroxide monohydrate | 3.0 | — | 25 | 24 | 35 |
| Example 44 | Di-t-butyl dicarbonate (1.05) | Heptanoic acid (1.05) | 1-Butanethiol (0.055) | Magnesium phosphate octahydrate | 3.0 | Lithium hydroxide monohydrate | 3.0 | — | 25 | 24 | 14 |
| Example 45 | Di-t-butyl dicarbonate (1.05) | Heptanoic acid (1.05) | 1-Butanethiol (0.055) | Magnesium chloride | 3.0 | Lithium hydroxide monohydrate | 3.0 | — | 25 | 24 | 83 |
| Example 46 | Di-t-butyl dicarbonate (1.05) | Heptanoic acid (1.05) | 1-Butanethiol (0.055) | Magnesium benzoate trihydrate | 3.0 | Lithiu hydroxide monohydrate | 3.0 | — | 25 | 24 | 78 |
| Example 47 | Di-t-butyl dicarbonate (1.05) | Heptanoic acid (1.05) | 1-Butanethiol (0.055) | Magnesium lactate trihydrate | 3.0 | Lithium hydroxide monohydrate | 3.0 | — | 25 | 24 | 70 |
| Example 48 | Di-t-butyl dicarbonate (1.05) | Heptanoic acid (1.05) | 1-Butanethiol (0.055) | Acetylacetone magnesium | 3.0 | Lithium hydroxide monohydrate | 3.0 | — | 25 | 24 | 72 |
| Example 49 | Di-t-butyl dicarbonate (1.05) | Heptanoic acid (1.05) | 1-Butanethiol (0.055) | Calcium hydroxide | 3.0 | Sodium carbonate | 3.0 | — | 25 | 24 48 | 59 84 |
| Example 50 | Di-t-butyl dicarbonate (1.05) | Heptanoic acid (1.05) | 1-Butanethiol (0.055) | Calcium oxide | 3.0 | Sodium carbonate | 3.0 | — | 25 | 24 48 | 40 66 |
| Example 51 | Di-t-butyl dicarbonate (1.05) | Heptanoic acid (1.05) | 1-Butanethiol (0.055) | Strontium oxide | 3.0 | Sodium carbonate | 3.0 | — | 25 | 24 48 | 4 16 |
| Example 52 | Di-t-butyl dicarbonate (1.05) | Heptanoic acid (1.05) | 1-Butanethiol (0.055) | Barium oxide | 3.0 | Sodium carbonate | 3.0 | — | 25 | 24 48 | 1 4 |

TABLE 6

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 53 | Di-t-butyl dicarbonate (1.00) | Heptanoic acid (1.00) | Cyclohexanethiol (0.091) | Magnesium hydroxide | 0.5 | Lithium hydroxide monohydrate | 0.25 | — | 25 | 24 | 94 |
| Example 54 | Di-t-butyl dicarbonate (1.00) | Heptanoic acid (1.00) | Cyclohexanethiol (0.091) | Magnesium hydroxide | 0.5 | Sodium carbonate | 0.25 | — | 25 | 24 | 98 |
| Example 55 | Di-t-butyl dicarbonate (1.00) | Heptanoic acid (1.00) | t-Butylmercaptan (0.091) | Magnesium hydroxide | 0.5 | Sodium carbonate | 0.25 | — | 25 | 24 | 87 |

TABLE 6-continued

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 56 | Di-t-butyl dicarbonate (1.00) | Heptanoic acid (1.00) | Benzenethiol (0.091) | Magnesium hydroxide | 0.5 | Lithium hydroxide monohydrate | 0.25 | — | 25 | 24 | >99 |
| Example 57 | Di-t-butyl dicarbonate (1.00) | Cyclohexane-carboxylic acid (1.00) | 1-Butanethiol (0.091) | Magnesium hydroxide | 0.5 | Lithium hydroxide monohydrate | 0.25 | — | 25 | 24 | 98 |
| Example 58 | Di-t-butyl dicarbonate (1.00) | Pivalic acid (1.00) | 1-Butanethiol (0.091) | Magnesium hydroxide | 0.5 | Lithium hydroxide monohydrate | 0.25 | — | 25 | 24 | >99 |
| Example 59 | Di-t-butyl dicarbonate (1.00) | Pivalic acid (1.00) | Methyl thioglycolate (0.091) | Magnesium hydroxide | 0.5 | Lithium hydroxide monohydrate | 0.25 | — | 25 | 24 | >99 |
| Example 60 | Di-t-butyl dicarbonate (1.00) | Pivalic acid (1.00) | 2-Mercapto-pyridine (0.091) | Magnesium hydroxide | 0.5 | Lithium hydroxide monohydrate | 0.25 | Dichloro-methane (45) | 25 | 24 | 99 |
| Example 61 | Di-t-butyl dicarbonate (2.00) | Pivalic acid (2.00) | 2-Mercapto-benzothiazole (0.091) | Magnesium hydroxide | 1.0 | Lithium hydroxide monohydrate | 0.5 | 1,4-Dioxane (90) | 25 | 24 | 95 |
| Example 62 | Di-t-butyl dicarbonate (1.00) | Benzoic acid (1.00) | 1-Butanethiol (0.091) | Magnesium hydroxide | 0.5 | Lithium hydroxide monohydrate | 0.25 | — | 25 | 24 | >99 |
| Example 63 | Di-t-butyl dicarbonate (2.00) | Benzoic acid (2.00) | 1,4-Butane-dithiol (0.091) | Magnesium hydroxide | 1.0 | Lithium hydroxide monohydrate | 0.5 | Toluene (40) | 25 | 24 | 95 |

TABLE 7

| | Compound represented by formula (I) (molar equivalent) | Carboxylic acid (molar equivalent) | Thiol (mol used) | Group 2 metal compound | Amount added (mol %) | Group 1 metal compound | Amount added (mol %) | Solvent (mL) | Reaction temperature (° C.) | Reaction time (h) | Yield of carboxylic acid thioester (%) |
|---|---|---|---|---|---|---|---|---|---|---|---|
| Example 64 | Di-t-butyl dicarbonate (1.00) | Adipic acid (0.50) | Benzenethiol (0.091) | Magnesium hydroxide | 1.0 | Lithium hydroxide monohydrate | 0.5 | 1,4-Dioxane (45) | 50 | 7 | (II) 85 (III) 15 |
| Example 65 | Di-t-butyl dicarbonate (1.00) | Monomethyl adipate (1.00) | Benzenethiol (0.091) | Magnesium hydroxide | 0.5 | Lithium hydroxide monohydrate | 0.25 | — | 25 | 24 | 99 |
| Example 66 | Di-t-butyl dicarbonate (1.00) | 3-Chloro-propionic acid (1.00) | Benzenethiol (0.091) | Magnesium hydroxide | 0.5 | Lithium hydroxide monohydrate | 0.25 | — | 25 | 24 | 98 |
| Example 67 | Di-t-butyl dicarbonate (1.05) | Methacrylic acid (1.05) | 1-Butanethiol (0.091) | Magnesium hydroxide | 0.5 | Lithium hydroxide monohydrate | 0.25 | — | 25 | 24 | 91 |
| Comparative Example 1 | Di-t-butyl dicarbonate (1.05) | Heptanoic acid (1.05) | 1-Butanethiol (0.091) | — | — | Lithium hydroxide monohydrate | 1.0 | — | 25 | 24 | 0 |
| Comparative Example 2 | Di-t-butyl dicarbonate (1.05) | Heptanoic acid (1.05) | 1-Butanethiol (0.055) | — | — | Lithium hydroxide monohydrate | 3.0 | — | 25 | 24 | 0 |
| Comparative Example 3 | Di-t-butyl dicarbonate (1.05) | Heptanoic acid (1.05) | 1-Butanethiol (0.055) | — | — | Sodium hydroxide | 0.5 | — | 25 | 24 | 0 |
| Comparative Example 4 | Di-t-butyl dicarbonate (1.05) | Heptanoic acid (1.05) | 1-Butanethiol (0.055) | — | — | Sodium phosphate | 0.5 | — | 25 | 24 | 0 |
| Comparative Example 5 | Di-t-butyl dicarbonate (1.05) | Heptanoic acid (1.05) | 1-Butanethiol (0.055) | — | — | Sodium carbonate | 3.0 | — | 25 | 24 48 | 0 0 |
| Comparative Example 6 | — | Heptanoic acid (1.05) | 1-Butanethiol (0.091) | Magnesium hydroxide | 0.5 | Lithium hydroxide monohydrate | 0.25 | — | 25 | 24 | 0 |

INDUSTRIAL APPLICABILITY

The method for producing carboxylic acid thioester of the present invention enables carboxylic acid thioester to be more efficiently and economically obtained with a smaller load on the environment than a conventional method. In addition, in the method for producing carboxylic acid thioester of the present invention, raw materials small in the load on the human body can be used, and a specified catalyst can be used to thereby provide carboxylic acid thioester at a high yield even at a normal temperature and a normal pressure (25° C., 1 atm).

The invention claimed is:

1. A method of producing a carboxylic acid thioester, comprising reacting a compound represented by the following formula (I), a carboxylic acid and a thiol in the presence of a catalyst including at least one Group 2 metal compound and at least one Group 1 metal compound, where the Group 1 metal compound is present in an amount of 0.01 to 50 moles per mole of the Group 2 metal compound:

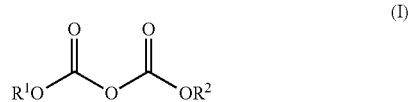

wherein $R^1$ and $R^2$ each independently represent a hydrocarbon group having 1 to 20 carbon atoms.

2. The method of producing a carboxylic acid thioester according to claim 1, wherein the catalyst includes 0.05 to 7 moles of the Group 1 metal compound per mole of the Group 2 metal compound.

3. The method of producing a carboxylic acid thioester according to claim 1, wherein 0.1 to 10 moles of the compound represented by the formula (I) and 0.1 to 10 moles of the carboxylic acid per mole of the thiol are reacted.

4. The method of producing a carboxylic acid thioester according to claim 1, wherein the compound represented by the formula (I) is di-t-butyl dicarbonate.

5. The method of producing a carboxylic acid thioester according to claim 1, wherein the carboxylic acid is (meth) acrylic acid.

6. The method of producing a carboxylic acid thioester according to claim 2, wherein the compound represented by the formula (I) is di-t-butyl dicarbonate.

7. The method of producing a carboxylic acid thioester according to claim 2, wherein the carboxylic acid is (meth) acrylic acid.

8. The method of producing a carboxylic acid thioester according to claim 3, wherein the compound represented by the formula (I) is di-t-butyl dicarbonate.

9. The method of producing a carboxylic acid thioester according to claim 3, wherein the carboxylic acid is (meth) acrylic acid.

10. The method of producing a carboxylic acid thioester according to claim 1, wherein the compound represented by the formula (I) is present in an amount of 0.5 to 5 moles per mol of the thiol.

11. The method of producing a carboxylic acid thioester according to claim 1, wherein the carboxylic acid is present in an amount of 0.5 to 5 moles per moles of the thiol.

12. The method of producing a carboxylic acid thioester according to claim 1, wherein $R^1$ and $R^2$ each independently represent a hydrocarbon group having 2 to 10 carbon atoms.

13. The method of producing a carboxylic acid thioester according to claim 1, wherein $R^1$ and $R^2$ each independently represent a hydrocarbon group having 3 to 7 carbon atoms.

14. The method of producing a carboxylic acid thioester according to claim 1, wherein $R^1$ and $R^2$ each independently represent one selected from the group consisting of an allyl group, a t-butyl group, a t-amyl group and a benzyl group.

* * * * *